United States Patent
Matsuo et al.

(10) Patent No.: US 10,441,198 B2
(45) Date of Patent: Oct. 15, 2019

(54) FACE DETECTION DEVICE, FACE DETECTION SYSTEM, AND FACE DETECTION METHOD

(71) Applicant: PANASONIC INTELLECTUAL PROPERTY MANAGEMENT CO., LTD., Osaka (JP)

(72) Inventors: Masatoshi Matsuo, Fukuoka (JP); Tsuyoshi Nakamura, Fukuoka (JP); Tadanori Tezuka, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 52 days.

(21) Appl. No.: 15/580,809

(22) PCT Filed: May 10, 2016

(86) PCT No.: PCT/JP2016/002278
§ 371 (c)(1),
(2) Date: Dec. 8, 2017

(87) PCT Pub. No.: WO2016/203698
PCT Pub. Date: Dec. 22, 2016

(65) Prior Publication Data
US 2018/0220939 A1     Aug. 9, 2018

(30) Foreign Application Priority Data
Jun. 19, 2015    (JP) .................................. 2015-123944

(51) Int. Cl.
*A61B 5/1171*     (2016.01)
*A61B 5/024*     (2006.01)
(Continued)

(52) U.S. Cl.
CPC ........ *A61B 5/1171* (2016.02); *A61B 5/02416* (2013.01); *A61B 5/742* (2013.01);
(Continued)

(58) Field of Classification Search
CPC ........... G06K 9/00228; G06K 9/00288; G06K 9/00536; G06K 9/00899; G06K 9/4652;
(Continued)

(56) References Cited

U.S. PATENT DOCUMENTS

| 6,172,706 B1 | 1/2001 | Tatsumi |
| 2015/0098632 A1* | 4/2015 | Monta ................ G06K 9/00295 382/118 |

(Continued)

FOREIGN PATENT DOCUMENTS

| JP | H08-294038 A | 11/1996 |
| JP | 2005-115460 A | 4/2005 |

(Continued)

OTHER PUBLICATIONS

John Guttag et al "Detecting Pulse from Head Motions in Video" IEEE 2013. (Year: 2013).*
(Continued)

*Primary Examiner* — Leon Flores
(74) *Attorney, Agent, or Firm* — Greenblum & Bernstein, P.L.C.

(57) ABSTRACT

Face detection device that detects a face from an image including a person. The device includes a processor and a memory including instructions that, when executed by the processor, cause the processor to perform operations including: receiving captured images by a camera, detecting one face region or more in the captured images, extracting vital information which includes an index indicating a living state of a face imaged in the face region, based on image data regarding the detected face region; and determining whether (Continued)

or not the face in the face region is in a living state, based on the vital information. The face region detector recognizes a face region corresponding to the face which is determined to be in the living state by the vitality determiner among the one face region or more, as a face region based on a living body.

9 Claims, 7 Drawing Sheets

(51) Int. Cl.
    *A61B 5/00*     (2006.01)
    *G06K 9/00*     (2006.01)
    *G06K 9/46*     (2006.01)

(52) U.S. Cl.
    CPC ..... *G06K 9/00228* (2013.01); *G06K 9/00288* (2013.01); *G06K 9/00536* (2013.01); *G06K 9/00899* (2013.01); *G06K 9/4652* (2013.01); *A61B 2576/02* (2013.01); *G06K 2009/00939* (2013.01)

(58) Field of Classification Search
    CPC .... A61B 5/1171; A61B 5/02416; A61B 5/742
    See application file for complete search history.

(56) References Cited

U.S. PATENT DOCUMENTS

| | | | |
|---|---|---|---|
| 2016/0150986 A1* | 6/2016 | Chen | G06T 7/0016 382/128 |
| 2016/0224825 A1 | 8/2016 | Tomita et al. | |
| 2017/0303862 A1 | 10/2017 | Nakamura et al. | |

FOREIGN PATENT DOCUMENTS

| | | |
|---|---|---|
| JP | 2013-150265 A | 8/2013 |
| JP | 2014-184002 A | 10/2014 |
| JP | 2014-219703 A | 11/2014 |

OTHER PUBLICATIONS

U.S. Appl. No. 15/580,925 to Tadanori Tezuka et al., filed Dec. 8, 2017.

U.S. Appl. No. 15/867,173 to Masao Hamada et al., filed Jan. 10, 2018.

Official Communication issued in International Patent Application No. PCT/JP2016/002278, dated Aug. 9, 2016, along with an English translation thereof.

* cited by examiner

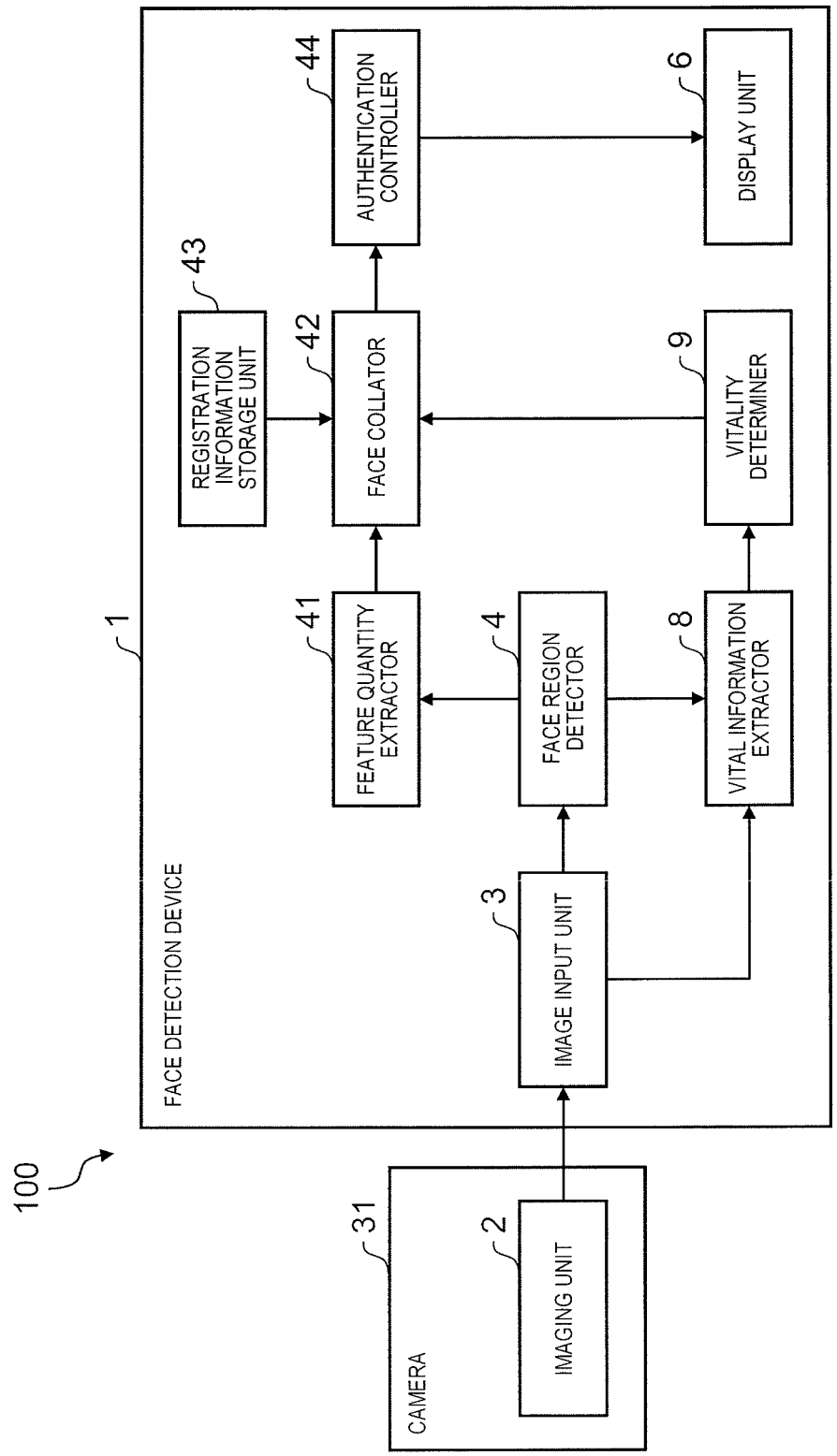

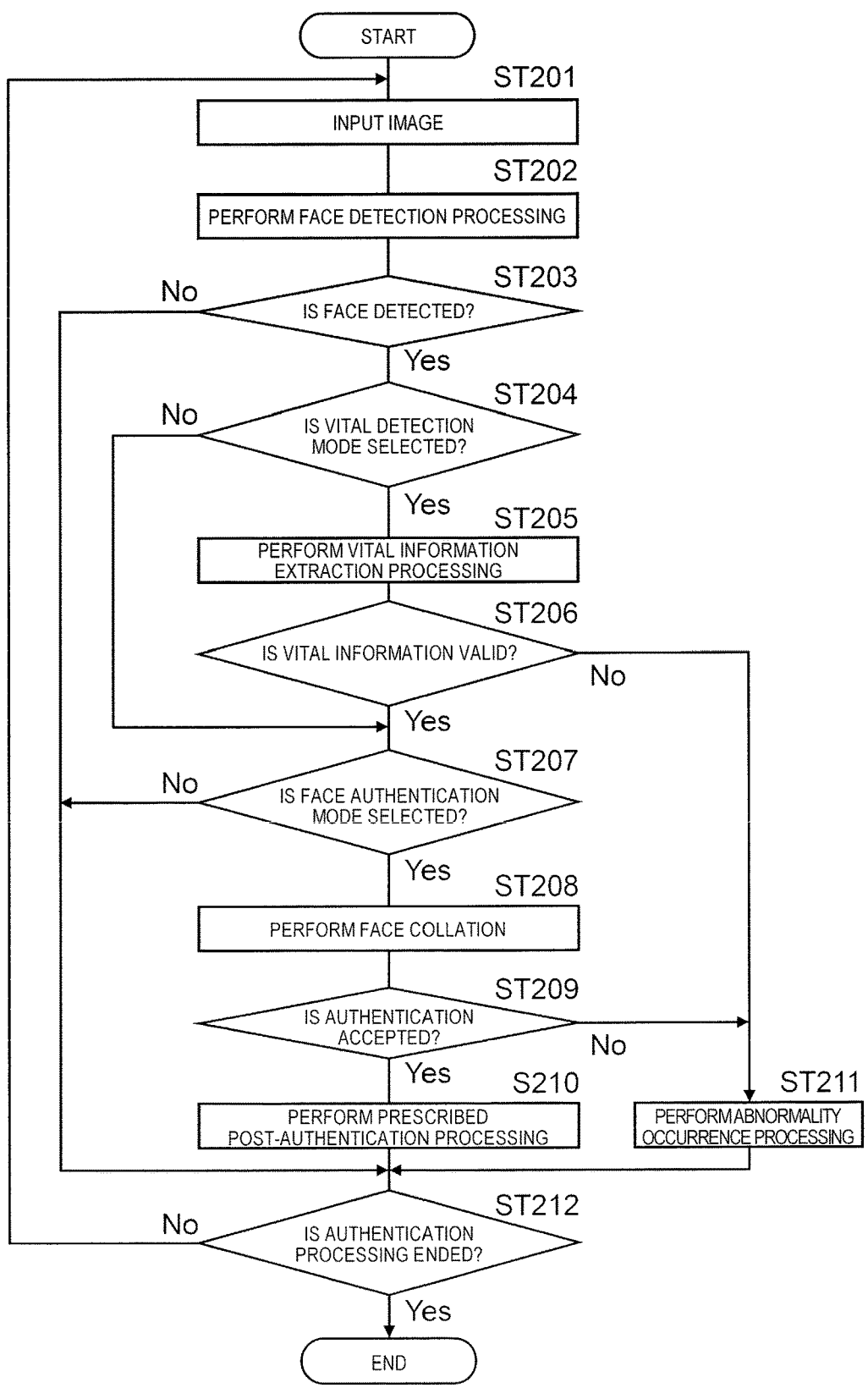

FACE DETECTION DEVICE, FACE DETECTION SYSTEM, AND FACE DETECTION METHOD

TECHNICAL FIELD

The disclosure relates to a face detection device, a face detection system, and a face detection method of detecting a face from an image including a person.

BACKGROUND ART

In the related art, in the field of performing capturing using a digital camera, authentication, or the like, a face detection technology in which the position and the like of a face is detected from the captured image is used, and various types of processing can be performed based on the face detection result.

For example, regarding camera capturing, a video camera having an automatic panhead or a capturing device as follows is known (see PTL 1 and PTL 2). The video camera having an automatic panhead detects the position of a face of a subject so as to automatically move a camera direction, and thus allows an image of the subject to be captured at a predetermined position on a screen. The capturing device detects the face of a subject included in an image and displays a trimmed image obtained by cutting out a region including the detected face. The capturing device displays the trimmed image at a predetermined position on an image displayed in the display unit, so as to be selectable, and thus allows a photographer to easily designate the major subject.

For example, regarding authentication, a face collation device is known (see PTL 3). The face collation device obtains a correlation value while a template which is previously prepared is moved in an image, and detects a region having the highest correlation value, as a face region of a person to be collated. Then, the face collation device performs personal authentication by combining face collation obtained a face image of the detected person to be collated, with face collation obtained by face temperature distribution of a person.

CITATION LIST

Patent Literature

PTL 1: Japanese Patent Unexamined Publication No. 8-294038
PTL 2: Japanese Patent Unexamined Publication No. 2013-150265
PTL 3: Japanese Patent Unexamined Publication No. 2005-115460

SUMMARY OF THE INVENTION

In the related art as disclosed in PTLS 1 to 2, there is a problem as follows. That is, in a case where an image as a target of face detection is acquired (captured), if an object (for example, photographic portrait stuck to a wall in the rear of a subject, or a face of a doll placed on the subject side) having features which are similar to those of the human face is provided around the subject, the object may be erroneously detected as the human face.

Regarding such a problem, in the related art as disclosed in PTL 3, it is considered that it is determined whether or not an object having a form which is similar to that of the human face is the face of a person, by using a dedicated sensor or the like, and thus an object other than the human face is excluded from a detection target. However, problems in that the configuration of the device is complicated and cost of the device is increased may occur.

The disclosure has been made considering such problems in the related art, and the main object of the disclosure is to provide a face detection device, a face detection system, and a face detection method in which an occurrence of a situation in which, in a case where a face is detected from an image including a person, an object other than the person is erroneously detected as the face of a living body is prevented.

According to the disclosure, a face detection device detects a face from an image including a person. The face detection device includes an image input unit, a face region detector, a vital information extractor, and a vitality determiner. The image input unit receives an input of captured images which include a person and are continuous in time. The face region detector detects one face region or more in the captured image. The vital information extractor extracts vital information which includes an index indicating a living state of a face imaged in the face region, based on image data regarding the face region. The vitality determiner determines whether or not the face in the face region is in the living state, based on the vital information. The face region detector recognizes a face region corresponding to the face which is determined to be in the living state by the vitality determiner among the one face region or more, as a face region based on a living body.

According to the disclosure, it is possible to prevent an occurrence of a situation in which, in a case where a face is detected from an image including a person, an object other than the person is erroneously detected as the face of a living body.

BRIEF DESCRIPTION OF DRAWINGS

FIG. 7 is a functional block diagram illustrating the face detection system according to the second exemplary embodiment.

FIG. 8 is a flowchart illustrating a flow of processing performed by the face detection device according to the second exemplary embodiment.

DESCRIPTION OF EMBODIMENTS

Figure 1:
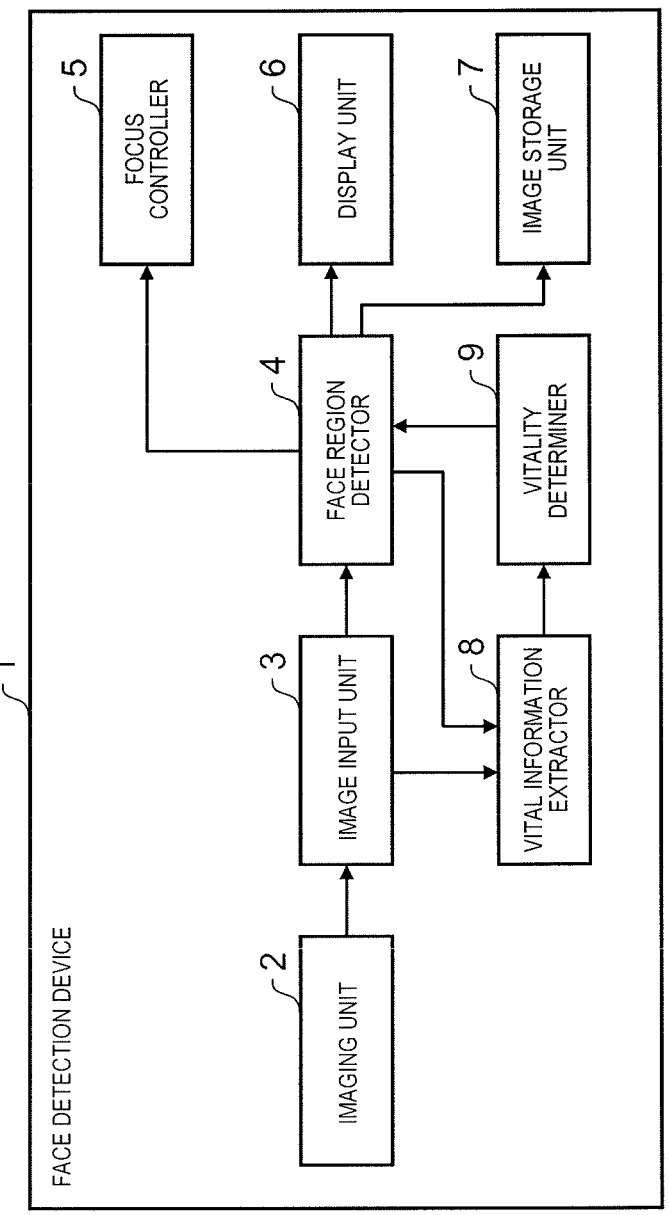
FIG. 1 is a functional block diagram illustrating a face detection device according to a first exemplary embodiment.

To solve the above problems, according to a first disclosure, there is provided a face detection device that detects a face from an image including a person. The face detection device includes an image input unit, a face region detector, a vital information extractor, and a vitality determiner. The image input unit receives an input of captured images which include a person and are continuous in time. The face region detector detects one face region or more in the captured image. The vital information extractor extracts vital information which includes an index indicating a living state of a face imaged in the face region, based on image data regarding the face region. The vitality determiner determines whether or not the face in the face region is in the living state, based on the vital information. The face region detector recognizes a face region corresponding to the face which is determined to be in the living state by the vitality determiner among the one face region or more, as a face region based on a living body.

According to the face detection device according to the first disclosure, a configuration in which a face region corresponding to the face which is determined to be in the living state among the one face region or more which are included in the captured image is recognized as a face region based on a living body is made. Thus, an occurrence of a situation in which, in a case where a face is detected from an image including a person, an object other than the person is erroneously detected as the face of a living body is prevented.

In the second disclosure, in the first disclosure, the vital information extractor estimates a pulse in the face imaged in the face region, based on the image data regarding the face region, and extracts the estimated pulse as the vital information.

According to the face detection device according to the second disclosure, a configuration in which it is determined whether or not the face in the face region is in the living state, based on the pulse is made. Thus, with a simple configuration, it is possible to recognize a face region based on a living body.

In the third disclosure, in the first or second disclosure, a display unit configured to display the captured image is further included. The face region detector performs image processing on the captured image displayed in the display unit. The image processing is performed for causing a user to distinguish a face region based on the living body from another face region among the one face region or more.

According to the face detection device according to the third disclosure, it is possible to cause a user to easily recognize a face region based on a living body. As a result, the user can perform a desired operation on the face region based on the living body.

In the fourth disclosure, in any one of the first to third disclosures, a face collator configured to collate the feature quantity of a face in the face region with information of a face, which is previously registered is further included. The face collator performs the collation only on the face which is determined to be in the living state by the vitality determiner.

According to the face detection device according to the fourth disclosure, a configuration in which face collation is performed only on the face (image) based on the living body is made. Thus, it is possible to prevent an occurrence of erroneous authentication by performing collation for a face which is not based on a living body.

In any one of the first to third disclosures, the fifth disclosure further includes a face collator configured to collate the feature quantity in the face in the face region with information of a face, which is previously registered. The face collator determines a result of the collation for a face which is determined to be not in the living state by the vitality determiner, to be invalid or discrepant.

According to the face detection device according to the fifth disclosure, a configuration in which a collation result for a face (image) which is not based on a living body is determined to be invalid or discrepant is made. Thus, it is possible to prevent an occurrence of erroneous authentication based on a collation result for a face which is not based on a living body.

According to a sixth disclosure, there is provided a face detection system which includes the face detection device according to any one of the first to fifth disclosures, and a camera configured to input the captured image to the face detection device.

According to the face detection system according to the sixth disclosure, a configuration in which a face region corresponding to the face which is determined to be in the living state among the one face region or more which are included in the captured image is recognized as a face region based on a living body is made. Thus, an occurrence of a situation in which, in a case where a face is detected from an image including a person, an object other than the person is erroneously detected as the face of a living body is prevented.

According to a seventh disclosure, there is provided a face detection method of detecting a face from a captured image including a person. The face detection method includes an image input step of receiving an input of captured images which include the person and are continuous in time, a face region detection step of detecting one face region or more in the captured image, a vital information extraction step of extracting vital information which includes an index indicating that a face imaged in the face region is in a living state, based on image data regarding the detected face region, and a vitality determination step of determining whether or not the face in the face region is in the living state, based on the vital information. In the face region detection step, a face region corresponding to the face which is determined to be in the living state in the vitality determination step among the one face region or more is recognized as a face region based on a living body.

According to the face detection method according to the seventh disclosure, a configuration in which a face region corresponding to the face which is determined to be in the living state among the one face region or more which are included in the captured image is recognized as a face region based on a living body is made. Thus, an occurrence of a situation in which, in a case where a face is detected from an image including a person, an object other than the person is erroneously detected as the face of a living body is prevented.

Hereinafter an exemplary embodiment according to the disclosure will be described with reference to the drawings.

First Exemplary Embodiment

Figure 2:
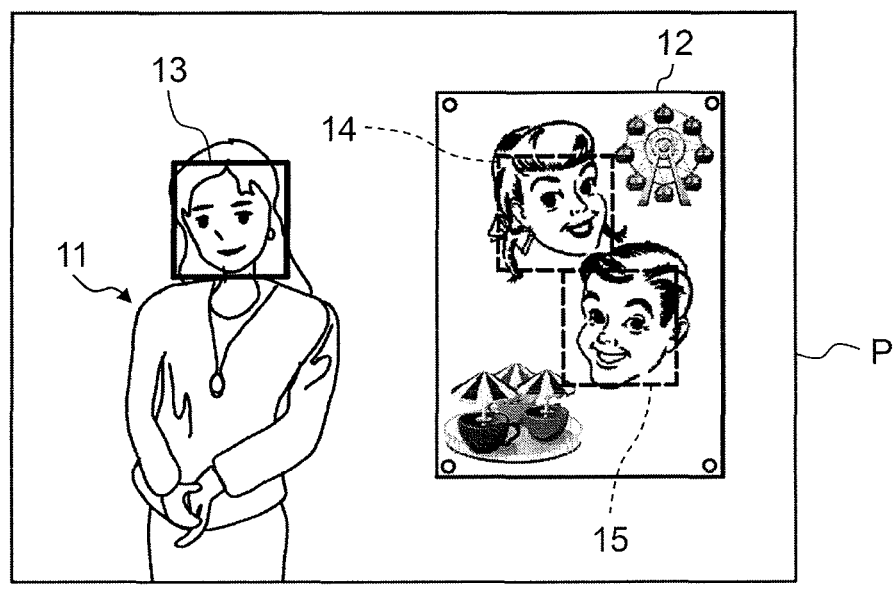
FIG. 2 is a diagram illustrating a first example of a face detection target of a face region detector according to the first exemplary embodiment.
Figure 3:
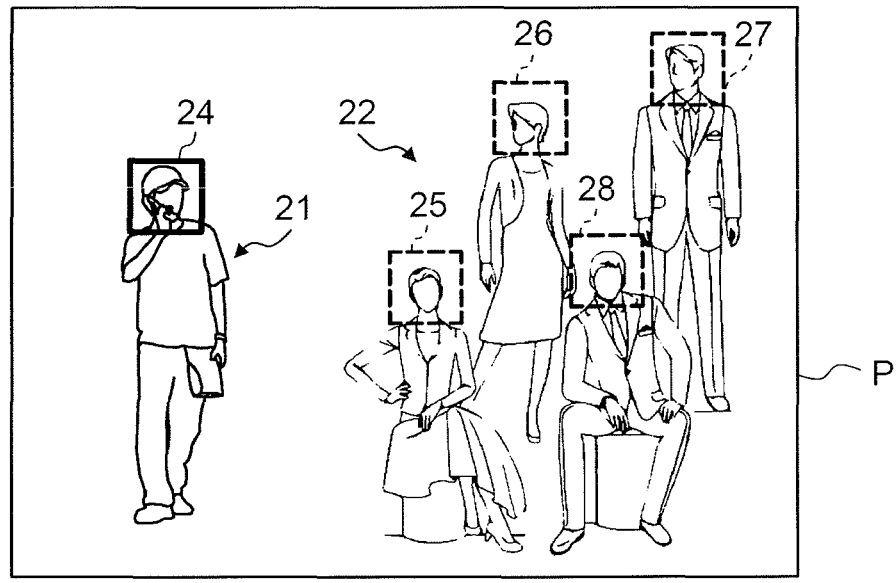
FIG. 3 is a diagram illustrating a second example of the face detection target of the face region detector according to the first exemplary embodiment.
Figure 4:
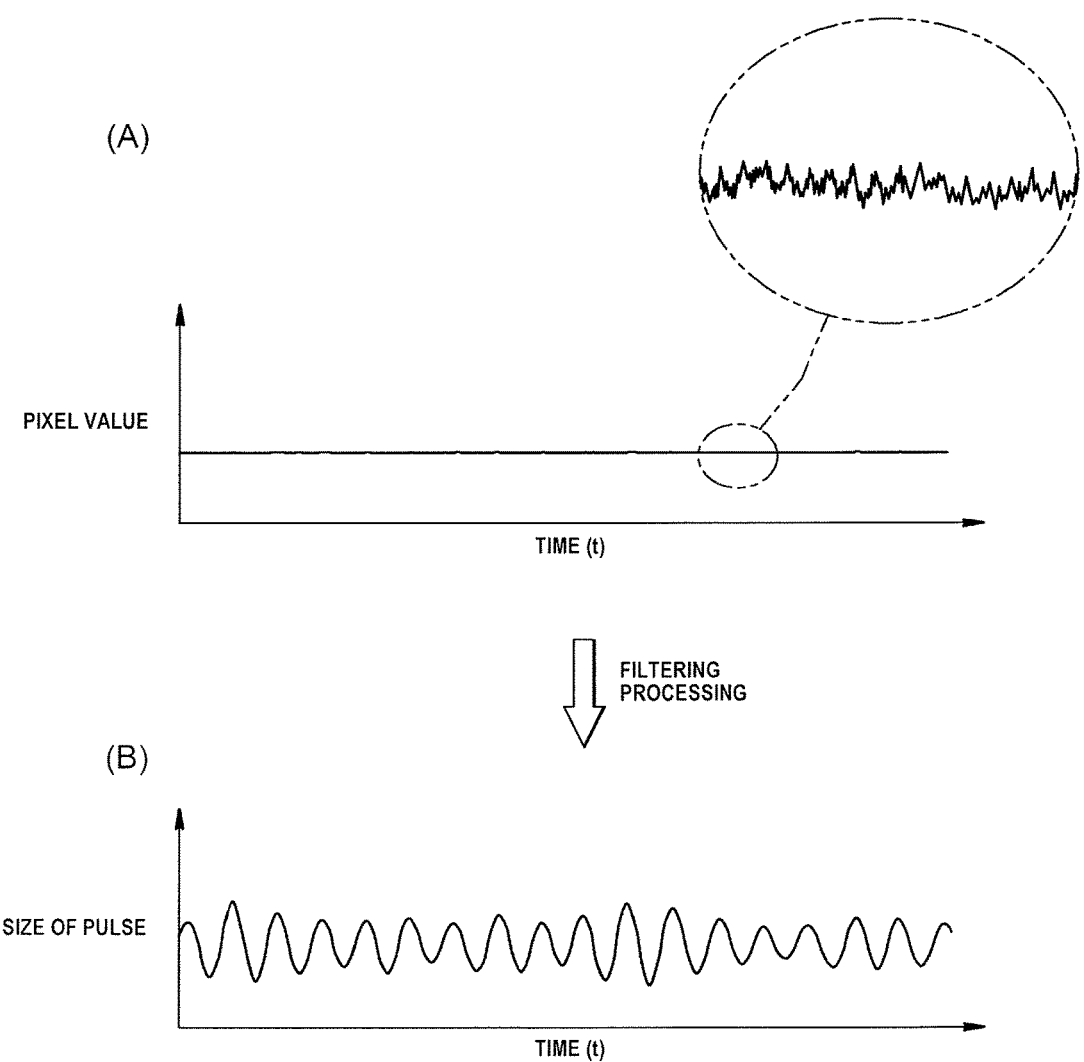
FIG. 4 is a diagram illustrating vital information extraction processing performed by a vital information extractor according to the first exemplary embodiment.

FIG. 1 is a functional block diagram of face detection device 1 according to a first exemplary embodiment of the disclosure. FIGS. 2 and 3 are diagrams illustrating first and second examples of a face detection target in face region detector 4, respectively. FIG. 4 is a diagram illustrating vital information extraction processing performed by vital information extractor 8.

As illustrated in FIG. 1, face detection device 1 includes imaging unit 2, image input unit 3, face region detector 4, focus controller 5, display unit 6, and image storage unit 7. Imaging unit 2 performs imaging of at least the face of a person, as a subject. Image input unit 3 receives an input of an image signal from imaging unit 2. Face region detector 4 detects one face region or more in captured images. Focus controller 5 controls an operation of a focus mechanism (not illustrated) which includes an optical system configured to input light for an image to imaging unit 2, based on the detection result of the face region. Display unit 6 displays the captured image input to image input unit 3, a face detection result obtained by face region detector 4, and the like. Image storage unit 7 stores the captured image.

Face detection device 1 includes vital information extractor 8 and vitality determiner 9 as constituent components for preventing an occurrence of a situation in which an object other than a person is erroneously detected as the face of a living body. Vital information extractor 8 extracts vital information in a face region based on image data regarding the face region detected by face region detector 4. Vitality determiner 9 determines whether or not the face in the face region is in a living state, based on the vital information. Here, the vital information includes at least an index indicating a living state of the face imaged in the face region.

Imaging unit 2 causes an imaging sensor (not illustrated) (CCD, CMOS, or the like) to perform imaging with light from a subject, and thus outputs an image signal obtained by converting the light for an image into an electrical signal, to image input unit 3. The light from a subject is obtained through the optical system. In imaging unit 2, well-known signal processing for the purpose of noise suppression, contour emphasis, or the like may be performed. Thus, captured images (data of frame image) which are continuous in time are sequentially input to image input unit 3.

Face region detector 4 performs face detection processing on each of the captured images, based on the well-known pattern recognition method (for example, matching with a template which is previously prepared). Thus, face region detector 4 detects and tracks a face region and acquires face detection information (coordinates, pixel values, and the like of the detected face region) regarding the face region. The face detection information acquired by face region detector 4 is transmitted to focus controller 5, display unit 6, vital information extractor 8, and the like along with data of the captured image. In the face detection processing performed by face region detector 4, well-known statistical learning methods using the feature quantity of a face may be used.

As will be described later in detail, in face detection device 1, an operation mode (referred to as a vitality detection mode below) in which only the face of a living body is detected in accordance with selection of a user may be performed. In the vitality detection mode, in a case where a face which is determined to be not in the living state by vitality determiner 9 is provided in the captured image, face region detector 4 excludes this face from the detection target.

For example, as illustrated in FIG. 2, in a case where person 11 and poster (object having a form which is similar to the face of a person) 12 which is stuck to a wall in the rear of a subject and includes a photographic portrait of a person are provided in captured image P, face region detector 4 detects only face region 13 of person 11 based on a living body, and excludes face regions 14 and 15 based on the photographic portrait in poster 12, which is not based on a living body, from the detection target.

For example, as illustrated in FIG. 3, in a case where person 21 and plurality (here, 4) of dolls (mannequins) 22 which are used for displaying costumes and are arranged around person 21 are provided in captured image P, face region detector 4 can detect only face region 24 of person 21 based on a living body, and exclude face regions 25 to 28 of plurality of dolls 22 which are not based on a living body, from the detection target.

Here, face regions 13 to 15 and 24 to 28 are indicated by rectangles. However, the face region detected by face region detector 4 may be variously changed. For example, a face region in which the contour of the face except for the head portion is used as an outer edge can be set.

Focus controller 5 acquires face detection information from face region detector 4. Thus, focus controller 5 may perform well-known auto-focus processing of controlling an operation of the focus mechanism on the basis (focus point) of the position of a face region in a captured image. In particular, in a case where the above-described vitality detection mode is performed, the face detection information from face region detector 4 includes only information based on the face of a living body. Thus, in focus controller 5, it is possible to appropriately focus on the face of a person even in a case where an object (face which is not based on a living body) having a form which is similar to the face of a person is provided in a captured image.

Vital information extractor 8 performs vital information extraction processing of extracting a pulse of a living body as vital information without contact with an extraction target (person). More specifically, regarding each pixel constituting a face region which is detected by face region detector 4 in captured images which are continuous in time, vital information extractor 8 calculates a pixel value (0 to 255 gradation) of, for example, each of RGB components, and generates time-series data of the representative value (here, average value of each pixel) as a pulse signal. In this case, time-series data can be generated base on a pixel value of only the green component (G) indicating that variation by pulsation occurs particularly largely.

The generated time-series data of the pixel value (average value) follows small variation (variation of a pixel value, which has a size of smaller than 1 gradation) based on a change of hemoglobin concentration in blood, as illustrated in FIG. 4(A), for example. Thus, vital information extractor 8 can perform, if necessary, well-known filtering processing (for example, processing by using a band pass filter in which a predetermined passband is set) on the time-series data based on the pixel value. Accordingly, as illustrated in FIG. 4(B), vital information extractor 8 can extract a pulse wave obtained by removing a noise component, as vital information. Vital information extractor 8 can calculate a pulse rate from a period between two peaks (or zero points) or more which are adjacent to each other in the pulse wave, and can set the calculated pulse rate as the vital information. The vital information extracted by vital information extractor 8 is transmitted to vitality determiner 9. Further, vital information extractor 8 can set a spectrum acquired by frequency analysis (fast Fourier transform) of the time-series data as illustrated in FIG. 4(A), as the vital information.

Vitality determiner 9 can determine whether or not a face in a face region is in a living state, based on information of pulse wave (see FIG. 4(B)) which is extracted as the vital information by vital information extractor 8. Here, vitality determiner 9 performs matching processing between the pulse wave extracted by vital information extractor 8 and a reference waveform of a pulse wave which is previously prepared, and thus vitality determiner 9 can determine whether or not a pulse is detected (that is, whether or not the detected face is in the living state. As another method, vitality determiner 9 may determine whether or not a face is in the living state, based on determination of whether or not an appropriate pulse rate is detected by vital information extractor 8. As still another method, vitality determiner 9 may determine whether or not the face is in the living state, based on a spectrum which is acquired as vital information by vital information extractor 8.

Face detection device 1 as described above may be realized as a video camera used for capturing an image of a person or the like. In this case, in face detection device 1, the captured image is sequentially input to image input unit 3 after activation of the device, and is displayed in display unit 6. A user operates a shutter button (recording start button), and thus the captured image is sequentially stored in image storage unit 7.

Although details are not illustrated, for example, face detection device 1 has a well-known hardware configuration which includes a central processing unit (CPU), a random access memory (RAM), a digital signal processor (DSP), a driver for the imaging sensor, an LCD, a memory card, and the like. The CPU collectively performs processing relating to imaging, control of peripheral devices, and the like, based on a predetermined control program. The RAM temporarily stores image data taken from the imaging sensor. The DSP performs predetermined image processing on image data. At least a portion of the function of each of the units in face detection device 1 illustrated in FIG. 1 may be realized by the CPU executing a predetermined control program relating to the disclosure. At least a portion of the function of face detection device 1 may be replaced by processing which is performed by different well-known hardware.

Figure 5:
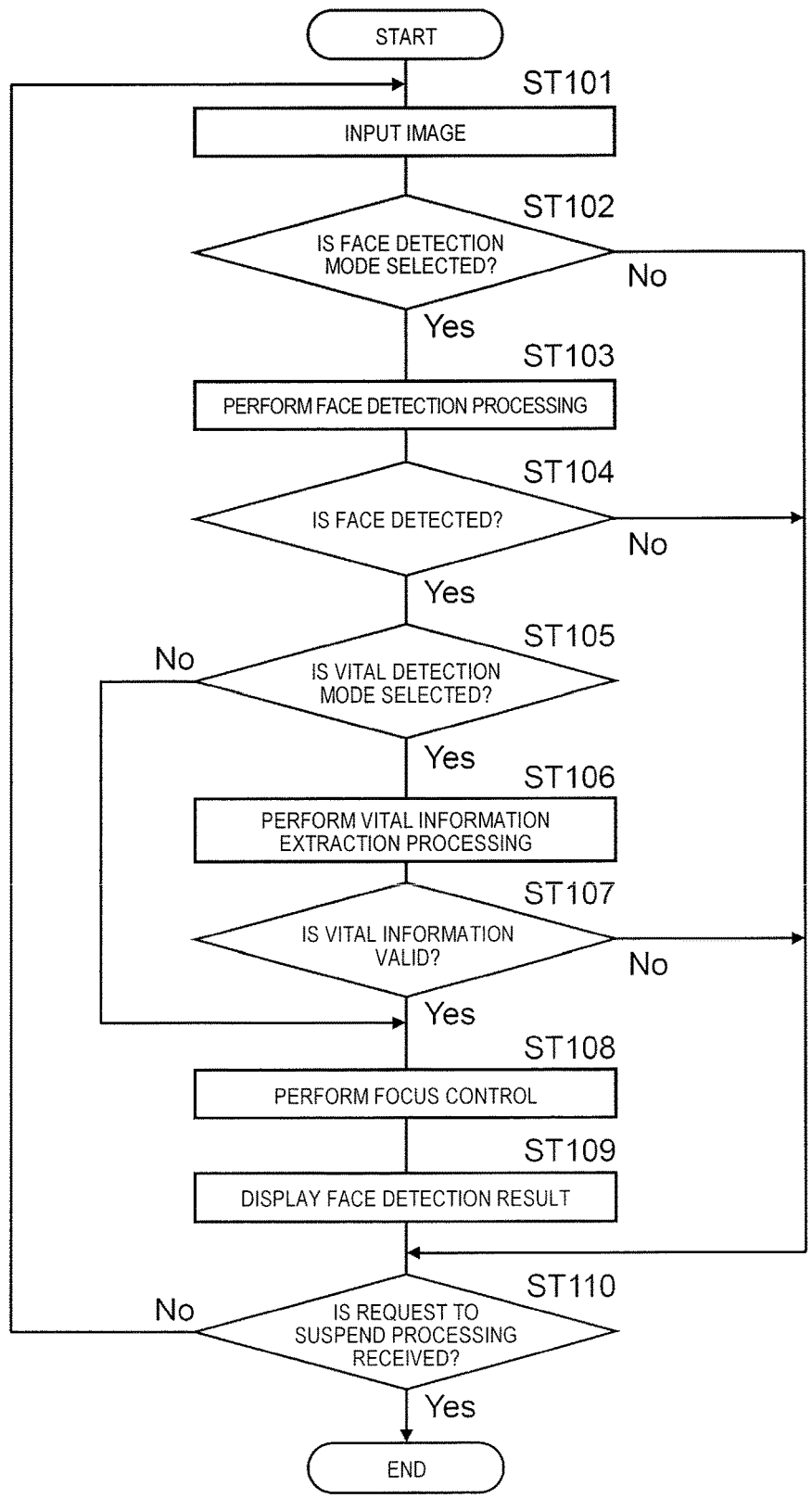
FIG. 5 is a flowchart illustrating a flow of processing performed by the face detection device according to the first exemplary embodiment.

FIG. 5 is a flowchart illustrating a flow of processing performed by face detection device 1 according to the first exemplary embodiment. In face detection device 1, imaging is started along with activation, and a captured image (frame image) is sequentially input to image input unit 3 from imaging unit 2 (ST101). In a case where a user of face detection device 1 selects an operation mode (referred to as a face detection mode below) in which face detection is performed (Yes in ST102), face region detector 4 performs the face detection processing (ST103).

Face detection device 1 determines whether or not a face region is detected by the face detection processing in Step ST103 (ST104). In a case where the face region is detected (Yes), face detection device 1 further determines whether or not the user selects the vitality detection mode (ST105).

In a case where the vitality detection mode is selected in Step ST105 (Yes), vital information extractor 8 extracts vital information (here, pulse) from each face region detected in Step ST103 (ST106). Then, vitality determiner 9 determines validity of the vital information extracted in Step ST106 (ST107). In the exemplary embodiment, in a case where it is determined that a face in a face region is in the living state, based on information regarding a pulse wave, which is extracted from the face region, vitality determiner 9 determines the vital information to be valid (Yes in ST107). In a case where it is determined that the face in the face region is not in the living state (that is, the face detected in Step ST103 is derived from an object having a form which is similar to the face of a person) based on the information regarding a pulse wave, vitality determiner 9 determines the vital information to be invalid (No in ST107).

In a case where it is determined that the vital information is valid (Yes) in Step ST107, focus controller 5 performs auto-focus processing based on the position of the face region detected in Step ST103 (ST108). The face detection result based on Step ST104 (for example, with reference to a frame which surrounds a face indicated as face region 13 in FIG. 2) is displayed along with the captured image in display unit 6 (ST109). Thus, it is possible to cause a user to easily recognize a face region based on a living body. As a result, the user may perform a desired operation on the face region based on a living body (for example, the user touches the face region so as to perform auto-focusing on the face region).

In a case where it is determined that the vital information is invalid (No) in Step ST107 when the vitality detection mode is performed, Steps ST108 and ST109 are not performed. Thus, it is possible to avoid an occurrence of a situation in which auto-focus control is performed based on a face region which is not based on a living body.

The above-described operations of Steps ST101 to ST109 are repeated until a processing suspension request is finally received through an operation of the user (for example, power-OFF operation, operation of completing capturing, and the like) (Yes in ST110). In a case where the user does not select performing of the face detection mode (No in ST102), the processes of Steps ST103 to ST109 are omitted. In a case where the user does not select the vitality detection mode (No in ST105), Steps ST106 and ST107 are not performed, and the auto-focus processing is performed based on the position of the face region (including a face region which is not based on a living body) detected in Step ST103 (ST108). For example, if the user separately performs an operation of pressing a shutter button (recording start button), the captured image after the auto-focus control is performed in Step ST108 is stored in image storage unit 7.

Second Exemplary Embodiment

Figure 6:
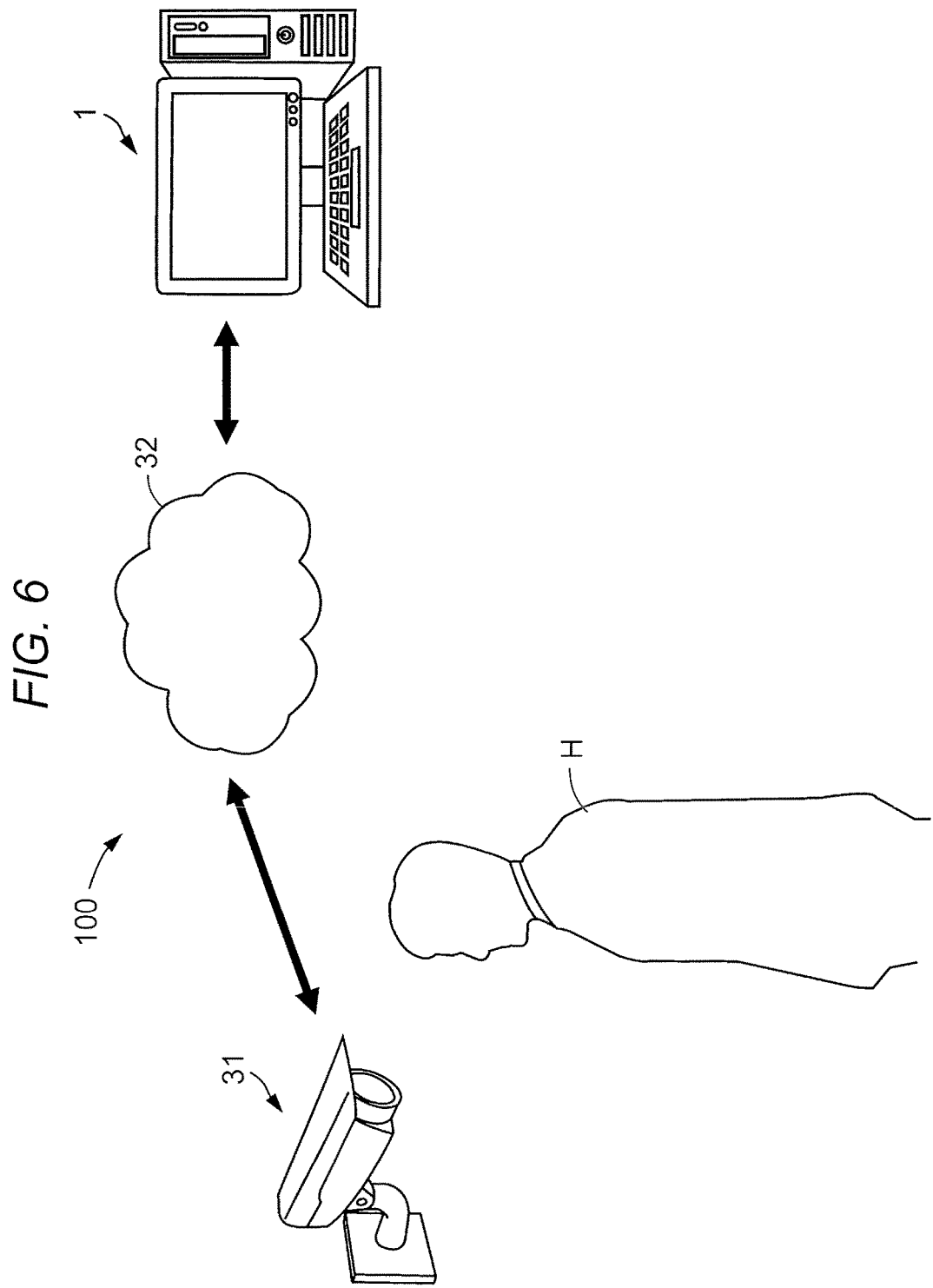
FIG. 6 is an overall configuration diagram illustrating a face detection system according to a second exemplary embodiment.

FIG. 6 is an overall configuration diagram illustrating face detection system 100 according to a second exemplary embodiment. FIG. 7 is a functional block diagram illustrating face detection system 100 according to the second exemplary embodiment. In FIGS. 6 and 7, constituent components which are similar to those in the above-described first exemplary embodiment are denoted by the same reference marks. In the second exemplary embodiment, it is assumed that an article which will be not particularly described below is similar to that in the above-described first exemplary embodiment.

As illustrated in FIG. 6, face detection system 100 includes camera 31 and face detection device 1. Camera 31 performs imaging of at least the face of person H as a subject. Face detection device 1 detects a face from a captured image obtained by capturing of camera 31. In the exemplary embodiment, face detection device 1 functions as a face authentication device that performs face detection, and perform face authentication based on the result of the face detection. Thus, face detection system 100 may function as a face authentication system. In face detection system 100, camera 31 and face detection device 1 are connected to each other via network 32 such as the Internet or a local area network (LAN), so as to be capable of communicating with each other. However, it is not limited thereto, and a configuration in which camera 31 and face detection device 1 are directly connected to each other by a well-known communication cable, so as to be capable of communicating with each other.

Camera 31 is a video camera having a well-known configuration. As illustrated in FIG. 7, camera 31 has imaging unit 2 which causes an imaging sensor (not illustrated) (CCD, CMOS, or the like) to perform imaging with light from a subject, and thus outputs an image signal obtained by converting the light for an image into an electrical signal, to face detection device 1. The light from the subject is obtained through a zoom lens. FIG. 6 illustrates only one camera 31. However, face detection system 100 may also have a configuration in which a plurality of cameras which are similar to each other are provided.

Face detection device 1 includes feature-quantity extractor 41, face collator 42, registration information storage unit 43, and authentication controller 44, in addition to image input unit 3, face region detector 4, display unit 6, vital information extractor 8, and vitality determiner 9 which, respectively, have functions similar to those in a case of the above-described first exemplary embodiment. Feature-quantity extractor 41 extracts the feature quantity of a face in the face region detected by face region detector 4. Face collator 42 performs face collation processing of collating the extracted feature quantity with information (referred to as registered face information below) of faces of people, which are previously registered. Registration information storage unit 43 stores the registered face information used in the collation. Authentication controller 44 performs, if necessary, predetermined post-authentication processing based on the collation result of the face, which is obtained by face collator 42.

Feature-quantity extractor 41 acquires face detection information from the face region detected by face region detector 4, by using a well-known method. Thus, feature-quantity extractor 41 detects feature points based on the shape of a face, relative positions of the eyes, the nose, the mouse, and the like, and the color of the face (skin), and the like in the face region, and extracts the feature quantity indicating the features. Here, it is preferable that the face region detected by face region detector 4 includes a face image on the front of person H.

Face collator 42 performs matching processing between the feature quantity extracted by feature-quantity extractor 41 and the registered face information (registered feature quantity), as the face collation processing. As a result obtained by the matching processing, in a case where it is determined that the extracted feature quantity coincides with a certain piece of the registered face information, face collator 42 transmits a notification of a message indicating that authentication is accepted, to authentication controller 44. In a case where it is determined that the extracted feature quantity does not coincide with any piece of the registered face information, face collator 42 transmits a notification of message indicating that authentication is rejected, to authentication controller 44.

In a case where the vitality detection mode is selected by the user of face detection system 100, face collator 42 acquires a result of determination (determination of whether or not the face in the face region is in the living state) performed by vitality determiner 9. Thus, face collator 42 can set only the face which is determined to be based on a living body (that is, to be in the living state) by vitality determiner 9, as a target of collation (matching processing). Alternatively, in a case where vitality determiner 9 determines that the face having the extracted feature quantity is not based on a living body, even though the extracted feature quantity coincides with a certain piece of the registered face information as a result of the matching processing, face collator 42 can determine the collation result to be invalid or discrepant.

With such a configuration, it is possible to prevent an occurrence of a situation in which, in a case where the vitality detection mode is selected, face collator 42 erroneously authenticates an object having a form which is similar to the face of a person (for example, the face of a doll, a photographic portrait of a person, which is not based on a living body, a mask created to be approximate to the face of a person, and the like).

If authentication controller 44 receives a notification of a message indicating that authentication is accepted, from face collator 42, authentication controller 44 performs post-authentication processing which is previously set. Such post-authentication processing is not particularly limited. For example, unlocking of a door of a security area, an output of information by using an image or sound in display unit 6, permission of an operation to an electronic device, and the like are included in the post-authentication processing. If authentication controller 44 receives a notification of a message indicating that authentication is rejected, from face collator 42, authentication controller 44 does not perform the post-authentication processing and records information regarding rejection of the authentication.

Face detection device 1 according to the above-described second exemplary embodiment may be configured, for example, from an information processing device such as a personal computer (PC). Although details are not illustrated, for example, the face detection device 1 has a hardware configuration which includes a central processing unit (CPU), a random access memory (RAM), a read only memory (ROM), a network interface, a monitor (image output device), a speaker, an input device, a hard disk drive (HDD), and the like. The CPU collectively performs various types of information processing, control of peripheral devices, and the like, based on a predetermined control program. The RAM functions as a work area of the CPU. The ROM stores data or the control program executed by the CPU. The network interface performs communication processing via a network. At least a portion of the function of each of the units in face detection device 1 illustrated in FIG. 7 may be realized by the CPU executing a predetermined control program. At least a portion of the function of face detection device 1 may be replaced by processing which is performed by different well-known hardware.

FIG. 8 is a flowchart illustrating a flow of processing performed by face detection device 1 according to the second exemplary embodiment. In face detection system 100, imaging by camera 31 is started along with activation, and Step ST201 which is similar to Step ST101 in FIG. 5 is performed. In face detection device 1, Steps ST202 to ST206 which are respectively similar to Steps ST103 to ST107 in FIG. 5 are performed.

Then, in a case where a user (manager) of face detection system 100 selects an operation mode in which face authentication is performed (Yes in ST207), face collator 42 performs the face collation processing using the feature quantity of the face (ST208). Then, if authentication controller 44 receives a notification of a message indicating that authentication is accepted, from face collator 42 (Yes in ST209), authentication controller 44 performs prescribed post-authentication processing (ST210).

In a case where the vital information is determined to be invalid in Step ST206 (it is determined that the detected face is not based on a living body) (No in ST206), authentication controller 44 performs predetermined abnormality occurrence processing (for example, report to the manager of face detection system 100, recording of a captured image at a time when abnormality occurs, and the like) (ST211).

The above-described Steps ST201 to ST211 are repeated until the entirety of the authentication processing is finally completed.

Hitherto, the disclosure is described based on the specific exemplary embodiments. However, the exemplary embodiments are just examples, and the disclosure is not limited to the exemplary embodiments. All of the constituent components of the face detection device, the face detection system, and the face detection method according to the disclosure, which are described in the exemplary embodiments are not necessary essential, and the constituent components thereof may be appropriately selected in a range without departing from at least the scope of the disclosure.

INDUSTRIAL APPLICABILITY

The face detection device, the face detection system, and the face detection method according to the disclosure can prevent an occurrence of a situation in which an object other than a person is erroneously detected as the face of a living body in a case where the face is detected from an image including the person, and are useful as a face detection device, a face detection system, and a face detection method of detecting a face from an image including a person.

REFERENCE MARKS IN THE DRAWINGS

1 FACE DETECTION DEVICE
2 IMAGING UNIT
3 IMAGE INPUT UNIT
4 FACE REGION DETECTOR
5 FOCUS CONTROLLER
6 DISPLAY UNIT
7 IMAGE STORAGE UNIT
8 VITAL INFORMATION EXTRACTOR
9 VITALITY DETERMINER
11, 21 PERSON
12 POSTER
13 TO 15 FACE REGION
22 DOLL
24 TO 28 FACE REGION
31 CAMERA
32 NETWORK
41 FEATURE-QUANTITY EXTRACTOR
42 FACE COLLATOR
43 REGISTRATION INFORMATION STORAGE UNIT
44 AUTHENTICATION CONTROLLER
100 FACE DETECTION SYSTEM
H PERSON
P CAPTURED IMAGE

The invention claimed is:

1. A face detection device that detects a face from an image including a person, the device comprising:
a processor; and
a memory including instructions that, when executed by the processor, cause the processor to perform operations including:
receiving captured images by a camera;
detecting at least one face region in the captured images;
collating a feature quantity of a face in a face region with information of a face which is previously registered;
determining whether a vitality detection mode has been selected, the vitality detection mode configured to recognize a face of a person in a living state but not a face of an object in a non-living state;
when the vitality detection mode is determined to have been selected:
extracting vital information which includes an index indicating the living state of a face imaged in the at least one face region, based on image data regarding the detected at least one face region;
determining whether or not the face in the at least one face region is in the living state, based on the vital information; and
when the face in the at least one face region is determined to be in the living state, recognizing a face region corresponding to the face which is determined to be in the living state among the at least one face region, as a face region of a living body, and the collating being performed by using of a feature quantity of the face in the face region corresponding to the face which is determined to be in the living state.

2. The face detection device of claim 1,
the instructions further include estimating a pulse in the face imaged in the face region, based on the image data regarding the at least one face region, and extracts the estimated pulse as the vital information.

3. The face detection device of claim 1, further comprising:
a display configured to display the captured images, and
the instructions further include performing image processing for causing a user to distinguish a face region based on the living body from another face region among the at least one face region, on the captured images displayed on the display.

4. The face detection device of claim 1,
wherein the collating is applied only on the face which is determined to be in the living state in a case where the face is determined to be in the living state.

5. The face detection device of claim 1, further comprising:
determining a face which is determined to be not in the living state, to be invalid or discrepant.

6. A face detection system comprising:
the detection device of claim 1; and
the camera configured to input the captured images to the face detection device.

7. The face detection device of claim 1, further comprising:
when the face in the at least one face region is determined not to be in the living state, not performing recognizing of a face region corresponding to the face which is determined not to be in the living state among the at least one face region.

8. The face detection device of claim 1,
wherein, when the vitality detection mode is not selected, recognizing a face region corresponding to the face which is determined not to be in the living state,
wherein the recognizing is performed on each of the at least one face region detected, and
wherein the at least one face region detected includes a face of a non-living object.

9. A face detection method of detecting a face from a captured image including a person, the method comprising:
receiving an input of captured images which include the person and are continuous in time;
detecting at least one face region in the captured images;
collating a feature quantity of a face in a face region with information of a face which is previously registered;
determining whether a vitality detection mode has been selected, the vitality detection mode configured to recognize a face of a person in a living state but not a face of an object in a non-living state;
when the vitality detection mode is determined to have been selected:
extracting vital information which includes an index indicating that a face imaged in the at least one face region is in the living state, based on image data regarding the detected at least one face region;

determining whether or not the face in the at least one face region is in the living state, based on the vital information; and when the face in the at least one face region is determined to be in the living state, recognizing a face region corresponding to the face which is determined to be in the living state among the at least one face region is recognized as a face region of the a living body, and the collating being performed by using of a feature quantity of the face in the face region corresponding to the face which is determined to be in the living state.

\* \* \* \* \*